United States Patent [19]

DeLuca et al.

[11] Patent Number: 4,481,198

[45] Date of Patent: Nov. 6, 1984

[54] VITAMIN D METABOLISM INHIBITOR

[75] Inventors: Hector F. DeLuca; Heinrich K. Schnoes, both of Madison, Wis.; John Y. Chu, Clinton, Miss.; Bruce D. Kabakoff, Bar Harbor, Me.

[73] Assignee: Wisconsin Alumni Research Foundation, Madison, Wis.

[21] Appl. No.: 579,620

[22] Filed: Feb. 13, 1984

[51] Int. Cl.$^3$ .......................... A61K 51/39; C07J 9/00
[52] U.S. Cl. .................................. 424/236; 260/397.2
[58] Field of Search ...................... 260/397.2; 424/236

[56] References Cited

U.S. PATENT DOCUMENTS 4,199,577  4/1980  Takeshita et al. .................. 424/236

OTHER PUBLICATIONS

Hey et al., J. Chem. Soc. 2881 (1950).

Primary Examiner—Elbert L. Roberts
Attorney, Agent, or Firm—Howard W. Bremer

[57] ABSTRACT

This invention provides a novel vitamin D derivative, namely a 24-oxime derivative of vitamin $D_3$, and a process for its preparation. The compound of this invention is an effective inhibitor of vitamin D-25-hydroxylation and markedly suppresses the formation of the physiologically active vitamin D metabolites. The compound would thus find use as an effective antagonist of vitamin D activation, and for treating hypercalcemic conditions resulting from metabolic, bone, or neoplastic diseases, or from vitamin D intoxication.

8 Claims, No Drawings

VITAMIN D METABOLISM INHIBITOR

DESCRIPTION

This invention was made with Government support under NIH grant number AM-14881 awarded by the Department of Health and Human Services. The Government has certain rights in this invention.

TECHNICAL FIELD

This invention relates to a novel vitamin $D_3$ derivative. Specifically, the invention relates to an oxime derivative of vitamin $D_3$. This derivative is a potent inhibitor of the enzymatic 25-hydroxylation of vitamin D compounds.

BACKGROUND

It is well known that for vitamin D to express biological activity in regulating calcium and phosphate metabolism, it must be activated by enzymatic hydroxylation. In the case of vitamin $D_3$ this metabolic activation sequence involves first a hydroxylation at carbon 25, occurring in liver tissue, and the resulting product, 25-hydroxyvitamin $D_3$, is then further hydroxylated in the kidney to the $1\alpha,25$-dihydroxyvitamin $D_3$ compound, which is generally considered the active hormonal form of the vitamin responsible for the regulation of calcium absorption and bone mineral deposition and resorption in the animal or human. Vitamin $D_2$ undergoes the exactly analogous activation sequence. Thus 25-hydroxylation represents the first step in vitamin D activation, and indeed all subsequent known metabolic conversions utilize the 25-hydroxy derivative as the required substrate. Blocking this 25-hydroxylation step would, therefore, prevent vitamin D activation, and hence would abolish or at least diminish the expression of vitamin D biological activity. Suppression of vitamin D activity would be desired in situations such as hypercalcemia resulting from bone or neoplastic disease or from vitamin D intoxication, and compounds that effectively inhibit vitamin D metabolism are thus useful therapeutic agents for the correction or treatment of such pathological hypercalcemic conditions.

Vitamin D-related compounds capable of suppressing the 25-hydroxylation of vitamin $D_3$ have been reported. These include, for example, a 25-aza-derivative (Onisko et al., J. Biol. Chem. 254, 3493 (1979)) and a 19-hydroxy-10,19-dihydro-vitamin $D_3$ compound (Paaren et al., Biochemistry 19, 5335 (1980)); high doses of these metabolic antagonists are required, however, to achieve even partial inhibition.

DISCLOSURE OF THE INVENTION

A new compound which effectively inhibits the 25-hydroxylation of vitamin $D_3$ has now been found. This compound is the oxime derivative of 24-oxo-vitamin $D_3$ and may be represented by the formula below

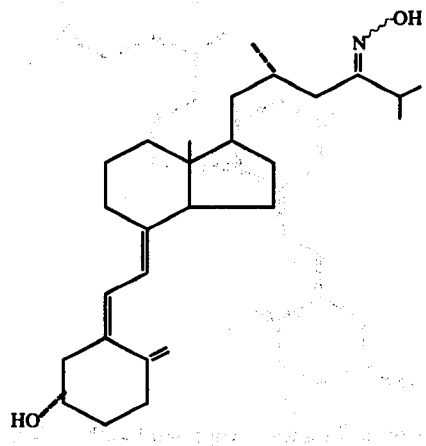

The compound is named herein vitamin $D_3$-24-oxime, or, in abbreviated form, 24-(NOH)$D_3$.

PREPARATION OF INHIBITOR

The above named compound is prepared from the known 24-oxocholesterol acetate (e.g. Riegel et al. J. Am. Chem. Soc. 66, 723 (1944); Hey et al. J. Chem. Soc. 2881 (1950)) having the structure shown below

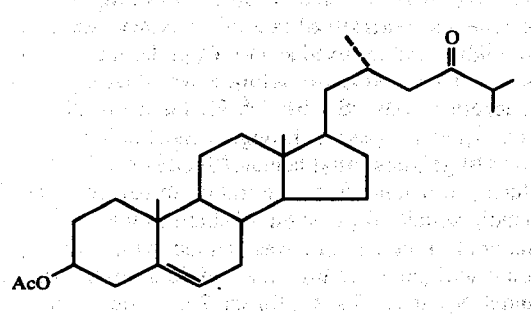

This material, under the general conditions of Hunziker and Müllner (Helv. Chim Acta 41, 70 (1958)) involving allylic bromination (at C-7) and dehydrobromination, is converted to the corresponding 5,7-diene having the structure below

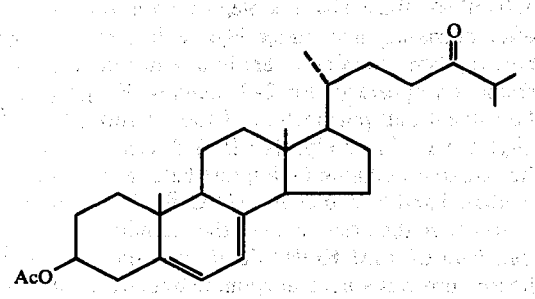

Irradiation of a solution of the above diene with ultraviolet light provides the corresponding previtamin $D_3$ analog, which is thermally isomerized under known and conventional conditions to give 24-oxo-vitamin $D_3$ acetate, from which after conventional hydrolysis of the 3β-acetate function there is obtained 24-oxo-vitamin $D_3$, characterized by the structure below

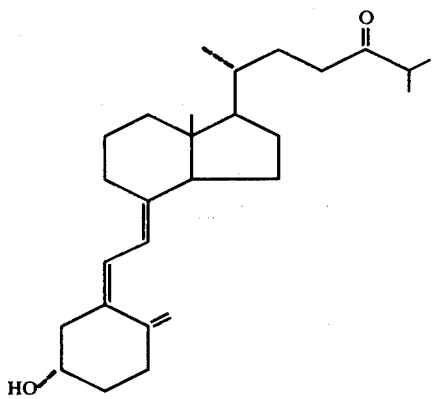

Treatment of the above compound with hydroxylamine then provides the desired oxime analog, vitamin $D_3$-24-oxime (24-(NOH)$D_3$) shown above.

The above described preparation of 24-(NOH)$D_3$ is more specifically illustrated by the following example.

EXAMPLE 1

A solution containing 80 mg of 24-oxocholesterol acetate, 50 mg of NaHCO$_3$, and 40 mg of dibromantin in 3 ml of Shellysolve B was heated to 70° C. under nitrogen for 30 min. The solution was cooled, the precipitate removed by filtration, and solvent was evaporated. The residue was redissolved in 2 ml of xylene and 0.2 ml of s-collidine and refluxed at 145° C. under nitrogen for 90 min. After cooling, the solution was diluted with benzene/ether, washed with 2% HCl and sat. NaCl solution, dried and passed through a short column of Silica Gel (10 g) using ethyl acetate/Shellysolve B (25:75) as eluent, to obtain after evaporation of solvent, a residue which contains the desired 5,7-diene as well as 4,6-diene material. This mixture was treated with p-toluenesulfonic acid (about 15 mg) in about 10 ml of dry dioxane, under N$_2$, at 70°–75° C., for ca. 2 hr. After cooling, the mixture was diluted with ether, washed with H$_2$O, and saturated NaHCO$_3$ solution, dried (Na$_2$SO$_4$) and solvent was evaporated. After purification of the residue by preparative TLC (Silica gel, ethyl acetate/Shellysolve B, 10:90) there was obtained the desired 5,7-diene (3β-acetoxy-5,7-cholestadien-24-one).

The above 5,7-diene was dissolved in diethyl ether (150 ml) and the ice bath-cooled solution, was irradiated (after degassing and under N$_2$) with a high pressure mercury lamp (Vycor filter) in a water cooled quartz irradiation apparatus for 2–3 minutes. Evaporation of the solvent and purification of the mixture (TLC, 5% ethyl acetate in Shellysolve B; 3 developments) gave the 24-oxo previtamin $D_3$ intermediate, which dissolved in ethanol and heated at 70°–80° C. for 3–4 hr under N$_2$ to isomerize the previtamin to the vitamin. To this solution, 3 ml of 0.1M KOH/MeOH was then added, and the mixture was stirred at room temperature for 20 hrs. After evaporation of solvent, addition of water, and extraction with ethyl acetate, the extracted material was purified by TLC (25% ethyl acetate in Shellysolve B) to obtain 24-oxo-vitamin $D_3$: UV $\lambda_{max}$ 265 nm; mass spectrum, m/z 398 (M$^+$, 30), 380 (6), 365 (13), 271 (6), 253 (15), 136 (100), and 118 (95); m/z calc. for $C_{27}H_{42}O_2$, 398.3185; found 398.3179; NMR (CDCl$_3$, 270 MHz) δ 0.54 (18-Me), 0.92 (d, J=5.6 Hz, 21-Me), 1.09 (d, J=7 Hz, 26,27-Me), 3.95 (m, 3-H), 4.82 and 5.05 (19E and 19Z-H), 6.04 (d, J=11 Hz, 7-H), 6.23 (d, J=11 Hz, 6-H).

A mixture of the above 24-oxo-vitamin $D_3$ and hydroxylamine hydrochloride in pyridine was stirred at room temperature for 42 hr. The solvent was removed and the residue was purified by preparative TLC (silica gel, 3% MeOH in CHCl$_3$) to obtain pure 24-oxime derivative (24-(NOH)$D_3$): UV $\lambda_{max}$ 265 nm, $\lambda_{min}$ 228 nm; mass spectrum, m/z 413 (M$^+$, 29), 398 (5), 397 (13), 396 (12), 380 (14), 278 (13), 262 (12), 136 (100), 118 (91), 98 (96), 43 (86). The compound can be obtained in crystalline form by crystallization from organic solvents. Suitable solvents for such purposes are, for example, absolute or aqueous low molecular weight alcohols, or alcohol/ether mixtures.

INHIBITION OF 25-HYDROXYLATION OF VITAMIN $D_3$ BY VITAMIN $D_3$-24-OXIME (24-(NOH)$D_3$)

The ability of 24-(NOH)$D_3$ to inhibit the 25-hydroxylation of vitamin $D_3$ was demonstrated in an in vitro microsomal enzyme system from rat liver. This system normally converts vitamin $D_3$ substrate to its metabolite, 25-hydroxyvitamin $D_3$ (25-OH-$D_3$), but in the presence of the inhibitor, 24-(NOH)$D_3$, this conversion is markedly suppressed.

The above result was demonstrated by the following experiment:

Animals.

Male rats, obtained as weanlings (Holtzman, Madison, WI) were maintained on a vitamin D-deficient 0.5% calcium and 0.3% phosphorus diet for 4–6 weeks prior to use for in vitro 25-hydroxylation assays. Animals were fasted 18 h to deplete glycogen stores prior to study.

Preparation of microsomes.

The microsomes were prepared by the method of Madhok and DeLuca (Biochem. J. 184, 491 (1979)). Livers were homogenized in 3 vol of 0.25M sucrose using a Potter-Elvehjem homogenizer fitted with a Teflon pestle. All centrifugation steps were done using a type 30 rotor and a Beckman L5-50 ultracentrifuge (Beckman Instruments, Lincolnwood, Ill.). A low-speed spin (650 g×15 min) was employed to remove the nuclei and cell debris and a 12,000 g×15 min spin was used to remove mitochondria.

The postmitochondrial supernatant was centrifuged at 105,000 g×60 min and the fluffy white layer at the top was removed by aspiration. The supernatant was then decanted and saved as the cytosolic fraction. The pellet was washed once in 0.25M sucrose and resuspended in the same solution to a protein concentration of 15 mg/ml, and used as the microsomal preparation.

Incubation procedures.

All incubations were performed with microsomal preparations using the general procedures of Bhattacharya and DeLuca (Arch. Biochem. Biophys. 160, 58 1974)). The incubation mixture contained 1 ml of microsomal suspension (15 mg protein), 4 ml of cytosolic fraction (~80 mg protein), an NADPH generating system, 25 mM phosphate buffer, pH 7.4, 5 mM ATP, and 10 mg of N,N'-diphenyl-para-phenylenediamine (DPPD) in a final volume of 10 ml. Inhibitor or the vehicle (10 μl EtOH) were preincubated at 37° C. for 10 min with the assay mixture prior to addition of substrate. The substrate was vitamin $D_3$ of the appropriate concentration with enough [$^3$H]vitamin $D_3$ added to provide 300–400 cpm/pmol. The incubations were stopped by addition of 30 ml of MeOH:CHCl₃ (2:1). Nonradioactive 25-OH-D₃ (~500 ng) was added to the mixture to monitor recoveries.

The work-up of the incubation mixture involved separation of the organic phase, and evaporation of solvent; the residue was then taken up in hexane:CHCl₃:MeOH (90:10:5) and applied to a Sephadex LH-20 column (Pharmacia, Piscataway, N.J.) (0.7×12 cm). The 25-OH-D₃ region (5-25 ml) was pooled, the solvent removed under vacuum and the residue applied to a Lipidex-5000 column (Packard Instruments, Lincolnwood, Ill.) (0.7×14 cm) equilibrated with hexane:CHCl₃ (90:10). The 25-OH-D₃ region (15-35 ml) was collected, the solvent removed, the residue dissolved in 4% of 2-propanol in hexane and injected into a Zorbax-SIL HPLC column (Dupont Co.) (0.46×25 cm) and eluted with the same solvent. The 25-OH-D₃ region (12-16 ml) was collected and chromatographed on a Zorbax-ODS HPLC (Dupont) column (0.46×25 cm) and eluted with 12% H₂O/MeOH. The radioactivity in the 25-OH-D₃ region was used as a measure of enzyme activity and the UV peak (254 nm) as a measure of recovery. Radioactivity was determined on a Packard Instruments 3255 liquid scintillation counter using a toluene counting solution with 0.4% p-bis-[2-(5-phenyloxazolyl)]-benzene and 0.03% dimethyl-1,4-bis-[2-(5-phenyloxazolyl)]-benzene. Recoveries were routinely 65-80%. The enzyme activity was expressed as picomole product (25-OH-D₃) produced per milligram protein per 2 hours.

Results obtained are shown in the Table below.

| [S] (nM) | Inhibitor | [I] | 25-OH—D₃ Formation (pmol/2h/mg protein) |
|---|---|---|---|
| 200 | None | — | 0.46 |
| 200 | None | — | 0.24 |
| 200 | None | — | 0.36 |
| 200 | 24-(NOH)D₃ | 500 nM | 0.09 |
| 200 | 24-(NOH)D₃ | 500 nM | 0.05 |

In the above Table, [S] is the concentration of substrate (vitamin D₃) and [I] is the concentration of inhibitor (24-(NOH)D₃) used.

The data given in the above Table show 24-(NOH)D₃ to be a highly effective inhibitor of the 25-hydroxylation of vitamin D₃. At a concentration of 500 nM (i.e. only 2½ times the concentration of substrate used) in the above described hydroxylation system, 24-(NOH)D₃ dramatically suppresses formation of 25-OH-D₃ from vitamin D₃ substrate.

Since vitamin D₂ is 25-hydroxylated (to 25-hydroxyvitamin D₂) by the same microsomal enzyme system, 24-(NOH)D₃ will also block the hydroxylation of vitamin D₂ and thus suppress the conversion of D₂ to its active metabolites. The foregoing results, indeed, indicate that 24-(NOH)D₃ should be effective for inhibiting the 25-hydroxylation of any vitamin D compound or analog.

Because of its strong inhibitory action on the 25-hydroxylation of vitamin D, the 24-oximo-D₃ derivative of this invention has utility as a pharmaceutical agent in situations where it is desired to suppress the metabolic activation of vitamin D. Suppression of vitamin D activation is specifically useful in order to alleviate, correct or prevent conditions of hypercalcemia which may result from a variety of disorders such as sarcoidosis, neoplastic disease, the milk-alkali syndrome or from vitamin D intoxication.

For therapeutic applications the compound of this invention may be administered orally or by injection or infusion. For such purposes the compound may be formulated as pills, tablets, capsules, together with suitable and pharmaceutically acceptable excipients, coloring matters, taste-modifiers, anti-oxidants and the like, or it may be formulated as solutions, emulsions, suspensions, or dispersions in suitable and innocuous solvents, or oils, with or without other acceptable excipients. Effective dosage amounts are between 0.01-10 mg per treatment, it being understood that the specific dosage administered is adjusted in accordance with the specific conditions to be treated and the condition and response of the subject.

We claim:

1. The compound having the formula

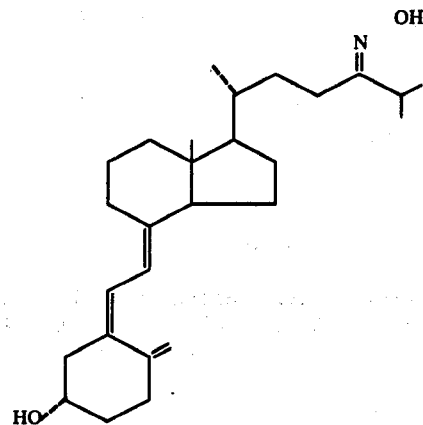

in amorphous or crystalline form.

2. A pharmaceutical composition comprising the compound of claim 1 and a pharmaceutically acceptable excipient.

3. A method for inhibiting metabolic vitamin D activation in animals which comprises administering an effective amount of the compound of claim 1.

4. A method for treating hypercalcemic conditions which comprises administering an effective amount of the compound of claim 1.

5. The method according to claim 4 where the hypercalcemic condition results from neoplastic disease.

6. The method according to claim 4 where the hypercalcemic condition results from sarcoidosis.

7. The method according to claim 4 where the hypercalcemic condition results from milk-alkali syndrome.

8. The method according to claim 4 where the hypercalcemic condition results from vitamin D intoxication.

* * * * *

UNITED STATES PATENT OFFICE
CERTIFICATE OF CORRECTION

Patent No. 4,481,198      Dated November 6, 1984

Inventor(s) Hector F. DeLuca et al

It is certified that error appears in the above-identified patent and that said Letters Patent are hereby corrected as shown below:

The formula in Column 6, Claim 1, should appear as shown below:

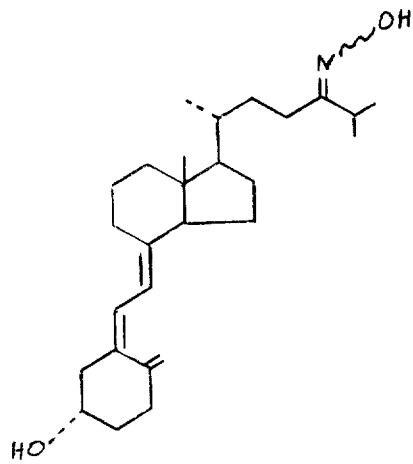

Signed and Sealed this

Ninth Day of April 1985

[SEAL]

Attest:

DONALD J. QUIGG

Attesting Officer      Acting Commissioner of Patents and Trademarks